US011513486B2

(12) United States Patent
Kupa et al.

(10) Patent No.: US 11,513,486 B2
(45) Date of Patent: Nov. 29, 2022

(54) SYSTEMS AND METHODS FOR INTELLIGENT DISINFECTION OF SUSCEPTIBLE ENVIRONMENTS BASED ON OCCUPANT DENSITY

(71) Applicant: Siemens Industry, Inc., Alpharetta, GA (US)

(72) Inventors: Timur Kupa, Crystal Lake, IL (US); Robert Baker, Olive Branch, MS (US); Pornsak Songkakul, Mequon, WI (US)

(73) Assignee: Siemens Industry, Inc., Alpharetta, GA (US)

( * ) Notice: Subject to any disclaimer, the term of this patent is extended or adjusted under 35 U.S.C. 154(b) by 68 days.

(21) Appl. No.: 16/515,865

(22) Filed: Jul. 18, 2019

(65) Prior Publication Data

US 2021/0018884 A1 Jan. 21, 2021

(51) Int. Cl.
*G05B 19/042* (2006.01)

(52) U.S. Cl.
CPC .... *G05B 19/042* (2013.01); *G05B 2219/2642* (2013.01)

(58) Field of Classification Search
CPC .... A61L 2/10; A61L 2202/14; A61L 2202/25; A61L 2/24; A61L 2209/111; A61L 2/0047; A61L 2/28; A61L 2202/16; A61L 2209/11; A61L 2209/16; A61L 9/00; G05B 15/02; G05B 2219/2642; G05B 2219/2614; G05B 19/048; G05B 19/042; F24F 11/30; F24F 11/62; F24F 2110/50; F24F 11/65; F24F 2120/12; F24F 3/1607; F24F 11/54; F24F 13/078; F24F 2003/1689; F24F 2120/10;
(Continued)

(56) References Cited

U.S. PATENT DOCUMENTS 8,877,124 B2 * 11/2014 Bergman .................. A61L 2/10
422/24
9,148,935 B2 9/2015 Mohan et al.
(Continued)

FOREIGN PATENT DOCUMENTS

WO 2013106077 7/2013

OTHER PUBLICATIONS

Enlighted Space Application, Enlighted, Inc., http://info.enlightedinc.com/rs/000-IKN-871/images/Space_SS_Rev08.pdf, Sunnyvale, CA, 2018, 2 pages.
(Continued)

*Primary Examiner* — Darrin D Dunn

(57) ABSTRACT

A building automation system may control ultraviolet lights to intelligently disinfect susceptible environments based on occupant density. The system comprises multiple occupancy sensors, a disinfection environment tracking engine, and an ultraviolet light control engine. The multiple occupancy sensors generate real time occupancy data associated with multiple objects detected within an area. The disinfection environment tracking engine determines real time occupant density of the multiple objects detected within the area based on the real time occupancy data generated by the multiple occupancy sensors. The ultraviolet light control engine controls operation of one or more ultraviolet lights to disinfect the area based on the real time occupant density determined by the disinfection environment tracking engine.

14 Claims, 5 Drawing Sheets

(58) Field of Classification Search
CPC ........... F24F 3/12; H05B 47/10; H05B 45/10; H05B 45/20; A61N 5/0624; A61N 5/06; A61N 2005/0626; A61N 2005/0652; G06K 9/00288; G06K 9/00671; G06K 9/00087; G06K 9/628; G06K 9/6293

See application file for complete search history.

(56) References Cited

U.S. PATENT DOCUMENTS

| | | | |
|---|---|---|---|
| 9,310,088 B2* | 4/2016 | Melikov | A61L 9/20 |
| 9,358,313 B2* | 6/2016 | Deal | H05B 47/18 |
| 10,178,737 B2 | 1/2019 | Mohan et al. | |
| 10,303,843 B2* | 5/2019 | Bitran | G16H 50/70 |
| 2007/0231194 A1* | 10/2007 | Jung | A61L 2/082 |
| | | | 422/3 |
| 2009/0265106 A1* | 10/2009 | Bearman | G06N 5/02 |
| | | | 701/300 |
| 2010/0032589 A1* | 2/2010 | Leben | B66B 11/024 |
| | | | 250/504 R |
| 2013/0085609 A1* | 4/2013 | Barker | H04L 67/12 |
| | | | 700/276 |
| 2015/0005951 A1 | 1/2015 | Srinivasan et al. | |
| 2015/0100330 A1* | 4/2015 | Shpits | G16H 50/80 |
| | | | 705/2 |
| 2015/0125937 A1* | 5/2015 | Peltz | G01N 15/0255 |
| | | | 435/286.1 |
| 2015/0177716 A1 | 6/2015 | Hyman et al. | |
| 2015/0234981 A1* | 8/2015 | Naidich | G16B 35/00 |
| | | | 506/8 |
| 2015/0279051 A1 | 10/2015 | Kovesi et al. | |
| 2015/0343104 A1* | 12/2015 | Maxik | G01S 17/04 |
| | | | 250/201.1 |
| 2016/0004237 A1 | 1/2016 | Mohan et al. | |
| 2016/0098024 A1 | 4/2016 | Purandare et al. | |
| 2017/0151359 A1* | 6/2017 | Clynne | A61L 2/10 |
| 2017/0246329 A1* | 8/2017 | Lloyd | A61L 2/084 |
| 2017/0246331 A1* | 8/2017 | Lloyd | A61L 2/084 |
| 2017/0312379 A1* | 11/2017 | Stibich | A61L 2/24 |
| 2018/0185533 A1 | 7/2018 | Lalicki et al. | |
| 2018/0264391 A1 | 9/2018 | Kirschman | |
| 2018/0296711 A1* | 10/2018 | Brais | A61L 2/10 |
| 2018/0339073 A1* | 11/2018 | Clynne | A61L 2/10 |
| 2019/0080796 A1* | 3/2019 | Greiner | G16H 40/20 |
| 2020/0016288 A1* | 1/2020 | Lalicki | A61L 9/20 |
| 2020/0145447 A1* | 5/2020 | Coffey | H04L 63/1425 |
| 2020/0176125 A1* | 6/2020 | Chatterjea | G16H 40/20 |
| 2020/0179544 A1* | 6/2020 | Ufkes | H05B 45/20 |
| 2020/0254125 A1* | 8/2020 | Lloyd | A61L 2/10 |
| 2020/0289686 A1* | 9/2020 | Janik | G01V 11/002 |
| 2020/0348038 A1* | 11/2020 | Risbeck | F24F 11/52 |
| 2021/0015959 A1* | 1/2021 | Goseki | A61L 9/20 |

OTHER PUBLICATIONS

PCT Search Report dated Oct. 9, 2020, for PCT Application No. PCT/US2020/038589, 13 pages.

PCT Search Report dated Jan. 28, 2021, for PCT Application No. PCT/US2020/038589, 19 pages.

* cited by examiner

SYSTEMS AND METHODS FOR INTELLIGENT DISINFECTION OF SUSCEPTIBLE ENVIRONMENTS BASED ON OCCUPANT DENSITY

FIELD OF THE INVENTION

Aspects of the present invention generally relate to building automation systems and, more particularly, systems and methods for intelligent disinfection of susceptible environments based on real time occupant density.

BACKGROUND

Building automation systems may be used to control environmental conditions in buildings. The systems provide the capability of managing many building management components from a central front-end interface or group of interfaces. The building management components may include building equipment for lighting, power, heating, ventilation, air conditioning, fire safety, and security. The building automation systems offer operational and sustainability benefits for building developers, managers, and occupants.

Buildings may include environments susceptible to infection or contamination. Healthcare associated infections, in particular, pose a significant issue in modern medical practice. Annual medical costs arising from healthcare associated infections are significant and continue to increase. Mechanisms to address healthcare associated infections include surface cleaning, personal hygiene, and, more recently, ultraviolet (UV) disinfection through UV lighting. Use of UV lights for UV disinfection, in combination with other medical cleaning processes, can result in marked decreases in healthcare associated infections. However, manual operation of UV lights can be cumbersome and inefficient. UV disinfecting lights also pose safety issues, as inadvertent exposure to UV lighting by patients, medical personnel, or other persons may cause significant bodily harm.

SUMMARY

Briefly, there is described implementations including systems, methods, devices, and logic that support disinfection of susceptible, i.e., possibly infected or contaminated, environments through use of ultraviolet (UV) lights that are controlled intelligently based on real time occupant density.

One aspect is a building automation system comprising multiple occupancy sensors, a disinfection environment tracking engine, and an ultraviolet light control engine. The multiple occupancy sensors are configured to generate real time occupancy data associated with multiple objects detected within an area. The disinfection environment tracking engine is configured to determine real time occupant density of the multiple objects detected within the area based on the real time occupancy data generated by the multiple occupancy sensors. The ultraviolet light control engine is configured to control operation of one or more ultraviolet lights to disinfect the area based on the real time occupant density determined by the disinfection environment tracking engine.

Another aspect is a method of a building automation system. Real time occupancy data associated with a plurality of objects detected within an area are generated at multiple occupancy sensors. Real time occupant density of the multiple objects detected within the area is determined at a disinfection environment tracking engine based on the real time occupancy data generated by the multiple occupancy sensors. Operation of one or more ultraviolet lights is controlled at an ultraviolet light control engine to disinfect the area based on the real time occupant density determined by the disinfection environment tracking engine.

Yet another aspect is a non-transitory machine-readable medium comprising storing instructions. When executed by a processor, the instructions cause a system to generate real time occupancy data, determine real time occupancy density of multiple objects, and control operation of one or more ultraviolet lights. The generated real time occupancy data are associated with the multiple objects detected within an area. The real time occupant density is based on the real time occupancy data generated by multiple occupancy sensors. The controlled operation of the ultraviolet light or lights disinfects the area based on the real time occupant density determined by the infection environment tracking engine.

BRIEF DESCRIPTION OF THE DRAWINGS

For a more complete understanding of the present disclosure, and the advantages thereof, reference is now made to the following descriptions taken in conjunction with the accompanying drawings, wherein like numbers designate like objects.

DETAILED DESCRIPTION

To facilitate an understanding of embodiments, principles, and features of the present invention, they are explained hereinafter with reference to implementation in illustrative embodiments. In particular, they are described in the context of intelligent disinfection of susceptible, i.e., possibly infected or contaminated, environments through use of ultraviolet (UV) lights. Embodiments of the present invention, however, are not limited to use in the described devices or methods.

The components and materials described hereinafter as making up the various embodiments are intended to be illustrative and not restrictive. Many suitable components and materials that would perform the same or a similar function as the materials described herein are intended to be embraced within the scope of embodiments of the present invention.

The disclosure herein may provide systems, methods, devices, and logic for intelligent control of UV lights to disinfect patient rooms based on occupant density. As described in greater detail below, a building automation system may track susceptible environments and automate intelligent operation of UV lights to disinfect patient rooms based on occupant density. Occupant density indicates the degree of occupancy of a particular area, such as a room, a building floor, or an otherwise designated area, which may be determined by the number of occupants within the particular area over a particular period of time. The building automation system may account for any number of various environmental and patient-based factors to intelligently control UV lights, doing so to increase UV light exposure in spaces susceptible to healthcare associated infections (e.g., hospital rooms). Described UV light control features may reduce instances of healthcare associated infections as UV lighting may be more efficiently and effectively operated as compared to manual operation.

As another benefit of the UV light control features described herein, cost savings may be achieved by optimizing operation parameters and activation times of controlled UV lights based on possible infection exposures, available disinfection times, patient-specific issues, etc. Further, the UV light control features described herein may track room occupancy in various ways, whether through occupancy sensors or patient real-time location data, automatically prioritizing safety by deactivating UV light operation upon detection that a susceptible environment is occupied.

These and other features and benefits of UV light control by a building automation system are described in greater detail herein.

Figure 1:
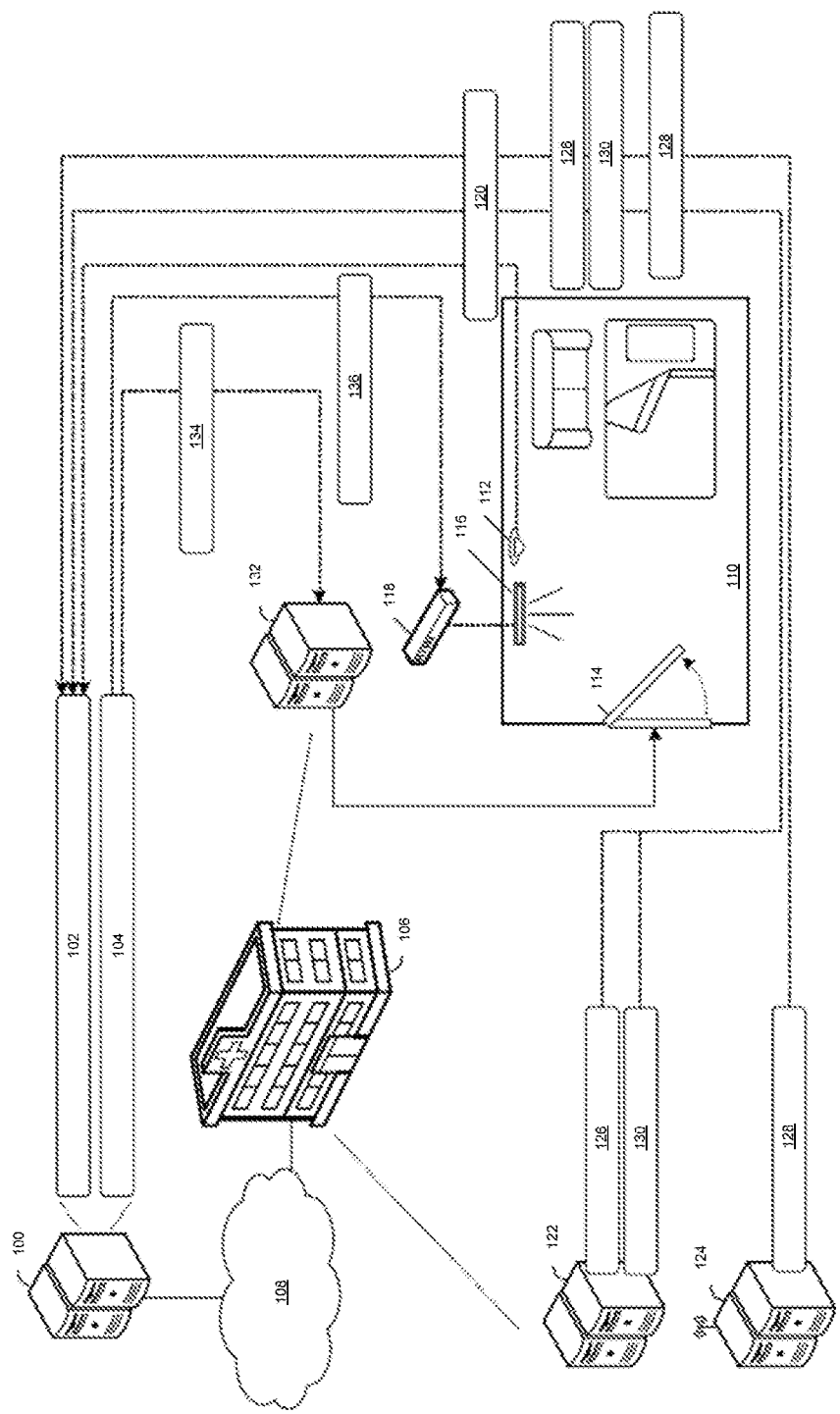
FIG. 1 represents an example of a health environment system that supports intelligent control of UV lights and room access to disinfect any number of susceptible environments.

FIG. 1 shows an example of a building automation system 100 that supports intelligent control of UV lights to disinfect any number of susceptible environments. The building automation system 100 may take the form of a computing system, including a single or multiple computing devices such as application servers, compute nodes, desktop or laptop computers, smart phones or other mobile devices, tablet devices, embedded controllers, and more. The building automation system 100 may include any system component that supports the control of building elements, such as heating, ventilation, air condition, lights and blinds, safety features, and any other building equipment. In some implementations, the building automation system 100 implements a unified building automation tool or building automation program through which multiple building controls are integrated, e.g., to increase energy and cost efficiencies, automate building operations, and more.

As described in greater detail herein, the building automation system 100 may support control of UV lights to disinfect susceptible environments of any number or type, e.g., susceptible areas and patient rooms. The building automation system 100 may automate the activation and deactivation of UV lights to disinfect patient rooms (or any other susceptible environment) based on occupant density and tracked environment data. Tracked environment data may include patient information such as patient room occupancy, patient treatment schedules, medical conditions of patients, real-time location data of patients, any other user-configurable factors, or combinations thereof. Tracked environment data may include non-patient information such as tracked information about facility personnel, facility maintenance, and clinical information (e.g., diseases and health care services). In some instances, the UV light control features described herein may provide disinfection of patient rooms with increased frequency or improved efficiency, which may result in a reduction in healthcare associated infections.

As an example implementation, the building automation system 100 shown in FIG. 1 includes a disinfection environment tracking engine 102 and a UV light control engine 104. The building automation system 100 may implement the engines 102, 104 (and components thereof) in various ways, for example as hardware and programming. The programming for the engines 102, 104 may take the form of processor-executable instructions stored on a non-transitory machine-readable storage medium and the hardware for the engines 102, 104 may include a processor to execute those instructions. A processor may take the form of single processor or multi-processor systems, and in some examples, the building automation system 100 implements multiple engines using the same computing system features or hardware components (e.g., a common processor or a common storage medium). A GUI, coupled directly or indirectly with the engines 102, 104, may include various components through which a user interfaces with the building automation system 100, such as a display, keyboard, mouse, touchscreen, etc.

In operation, the disinfection environment tracking engine 102 may track a combination of building environment data and patient data relevant to a susceptible environment, and the UV light control engine 104 may control UV lights based on the tracked data. In a hospital or other healthcare setting, the disinfection environment tracking engine 102 may access patient room data indicative of a state of a patient room of a patient, medical data of the patient that specifies a medical condition of the patient, and real-time location data of the patient. In such examples, the UV light control engine 104 may control operation of a UV light to disinfect the patient room based on the patient room data, the medical data of the patient, and the real-time location data of the patient.

Some example features relating to UV light control are presented in greater detail next. Many of the UV light control features presented herein are described via a patient room as an illustrative susceptible environment. However, a building automation system may consistently implement any of the described UV light control features for other susceptible environments as well, such as hospitality spaces (e.g., hotel rooms), food preparation facilities, cruise ships or other entertainment spaces, school classrooms, mixed office spaces, or any other environment in which UV lighting can be used for disinfection.

For some embodiments, UV light control by the building automation system 100 may be based on patient room data. An example susceptible environment is depicted in FIG. 1 as a hospital 106. Although shown as physically remote to the hospital 106, in some examples the building automation system 100 is located within or as part of the hospital 106, whether in part or in whole.

The building automation system 100 may provide control capabilities for various building elements of the hospital 106. Communications between the building automation system 100 and the hospital 106 may be supported by the network 108. The network 108 may take the form of any combination of one or more communication networks (or sub-networks) and supporting components by which the building automation system 100 may interact with specific building elements of the hospital 106. As such, the network 108 may include the Internet, proprietary backend communication systems, building device interfaces, and the like.

In the example shown in FIG. 1, the hospital 106 includes a patient room 110. The patient room 110 may be any physical space assigned to a patient, such as a hospital room, a treatment area, an allocated section of a hospital wing, etc. Accordingly, the patient 110 may include various building elements such as a bed, furniture, medical equipment or devices, lighting and blinds, tables, televisions, etc. In the particular example shown, the patient room 110 includes a patient bed, a couch, an occupancy sensor 112, a door 114, and a UV light 116. The UV light 116 may be any UV lighting device or building element that supports room disinfection. In that regard, the UV light 116 may provide sterilization capabilities through UV light emanation. Operation of the UV light 116 may be set through a UV light controller 118, which may include any circuitry that controls UV light 116 activation or deactivation, and support configuration of specific settings or characteristics of the emitted UV light (e.g., intensity, frequency, modulation, or any other UV light operation parameters).

The building automation system 100 may support automated operation of the UV light 116 in the patient room 110. In particular, the building automation system 100 may intelligently automate operation of the UV light 116 by communicating activation, parameter configuration, or deactivation instructions to the UV light controller 118. Such instructions may be issued by the building automation system 100 based on room occupancy schedules, other preset schedules, room occupancy states, room occupancy density, and other factors, doing so while managing power and energy consumption of the UV light 116 (e.g., by identifying opportunities to reduce excess energy consumption for the disinfection process). In doing so, the building automation system 100 may increase disinfection efficiency, optimize disinfection time, reduce building costs, or provide other benefits.

In some implementations, the building automation system 100 controls operation of the UV light 116 based on occupancy of the patient room 110. To track occupancy, the disinfection environment tracking engine 102 may acquire patient room data for the patient room 110, which may include any data indicative of a state of a patient room of a patient. For instance, the disinfection environment tracking engine 102 may access an occupancy status of the patient room from the occupancy sensor 112 in the patient room 110, whether by polling the occupancy sensor 112 or having occupancy status changes pushed from the occupancy sensor 112. The occupancy state or status includes an occupant density that indicates the degree of occupancy of a particular area by one or more people based on the number of occupants within the particular area over a particular period of time. For example, the occupant density may increase as the number of people within the particular area for a particular time period increases. Examples of the particular area include, but are not limited to, a room, a floor of a building, a hallway, a partitioned area, an open room, or other designated area. It should be noted that people or occupants may be referred to as objects herein because the building automation system and its components may identify a person or occupant as a type of object. In the example shown in FIG. 1, the disinfection environment tracking engine 102 obtains an occupancy data 120 from the occupancy sensor 112, which may include data indicative of an occupancy state of the patient room 110.

The building automation system 100 may activate the UV light 116 on an opportunistic basis at times (e.g., whenever) the patient room 110 is unoccupied. Based on the occupancy status, which includes the occupant density, of the patient room 110, the UV light control engine 104 may activate or deactivate the UV light 116, for instance by issuing activation or deactivation commands to the UV light controller 118. For these embodiments, activation or deactivation commands from the UV light control engine 104 may be included as control instructions, e.g., as depicted in FIG. 1 as the control instructions 136. When the occupancy status indicates the patient room 110 is unoccupied, the UV light control engine 104 may activate the UV light 116 to disinfect the patient room. When the occupancy status accessed from the occupancy sensor 112 indicates the patient room 110 is occupied (whether by the patient, another person, or multiple people), the UV light control engine 104 may control the UV light 116 based on the occupant density by reducing power and/or reducing active time or frequency of the UV light. Accordingly, the UV light control engine 104 may activate, deactivate, or modify the UV light 116 for room disinfection based on a present occupant density of the patient room 110, e.g., as tracked by the occupancy sensor 112.

For some embodiments, the UV light control engine 104 may utilize a determined occupancy status, which includes the occupant density, in combination with other factors to control operation of the UV light 116. An example of UV light control by a building automation system 100 based on patient room data, such as patient schedules, and real-time location data of a patient is further shown in FIG. 1. To support such operation, the disinfection environment tracking engine 102 may access susceptible environment or patient data from various sources to support intelligent control of the UV light 116. As examples, the hospital 106 may include various systems that track relevant patient data that the UV light control engine 104 may utilize to intelligently control UV lighting. For example, the hospital 106 includes a patient information management system 122 and a patient real-time location system 124.

The patient information management system 122 may store patient or other medical information of any type. Such patient/medical information may include electronic medical records of patients, disease and treatment history, admission and discharge records, prescription schedules, billing systems, procedural strategies, medical literature systems, disease databases, and more. To support such data warehousing, the patient information management system 122 may itself incorporate or include multiple disparate information systems, including as examples patient admission/discharge/transfer (ADT) systems, patient bed management systems (BMS), billing systems, registration and scheduling systems, occupancy schedules, and more.

The UV light control engine 104 may operate the UV light 116 based on occupancy periods determined from occupancy schedules for the patient room 110. An occupancy schedule may refer to any data, listing, or other time-specification mechanism indicative of scheduling for the patient room 110 or relevant personnel that access the patient room 110 (e.g., the patient, medical staff, cleaning staff, visitors, etc.). FIG. 1 shows one example of an occupancy schedule stored by the patient information management system 122 through a patient treatment schedule 126 for a patient, which the disinfection environment tracking engine 102 may retrieve for a patient assigned to the patient room 110.

The UV light control engine 104 may analyze the patient treatment schedule 126 (or any other occupancy schedule) to determine occupied and unoccupied time periods for the patient room 110. For instance, the UV light control engine 104 may identify an assigned occupancy period from the patient information management system 122 during which a patient is assigned to the patient room 110 (e.g., via patient-to-room assignment data tracked by an ADT system or system module implemented by the patient information management system 122). During the assigned occupancy period, the UV light control engine 104 may extract time periods from the patient treatment schedule 126 during which the patient is scheduled for treatments or other medical activity outside of the patient room 110. The UV light control engine 104 may interpret any such scheduled time periods during which the patient is not scheduled to be present in the patient room 110 as unoccupied time periods for the patient room 110. Non-scheduled times may be interpreted by the UV light control engine 104 as occupied time periods during which the patient is scheduled or expected to be present in the patient room 110.

As illustrative example, the disinfection environment tracking engine 102 may access patient admission date/time data and a patient treatment schedule 126 from the patient information management system 122, specifically for the patient assigned to the patient room 110. The obtained patient information may indicate a patient admission time of 9:00 am and a CT scan scheduled for 1:00 pm-2:00 pm on the same day. Accordingly, the UV light control engine 104 may determine the time period from 9:00 am-1:00 pm as an occupied time period and the time period from 1:00 pm-2:00 pm as an unoccupied time period for the patient room 110 based on the accessed patient treatment schedule 126. In a similar manner, the UV light control engine 104 may parse or extract other unoccupied and occupied time periods from the patient treatment schedule 126.

The UV light control engine 104 may control operation of the UV light 116 in the patient room 110 according to the unoccupied time periods extracted from the patient treatment schedule 126. During the determined unoccupied time periods, the UV light control engine 104 may activate the UV light 116 to disinfect the patient room 110 and deactivate the UV light 116 during the determined occupied time periods in the patient treatment schedule 126.

While a patient treatment schedule 126 is provided as an example source (e.g., occupancy schedule) from which the UV light control engine 104 may determine unoccupied time periods for the patient room 110, other data sources may be likewise utilized to determine scheduled occupancy of the patient room 110. Other example sources include visitation hours to the patient room 110 (or the assigned patient), active visitations (e.g., when a visitor to the patient room 110 has been logged into a visitation system but not yet logged out), visitation schedules of medical staff (e.g., medical rounds or scheduled check-ins by nursing staff), cleaning staff schedules, etc., each for which the UV light control engine 104 may treat as an occupied time period for the room 110. For unoccupied time periods determined from any such sources, the UV light control engine 104 may activate the UV light 116 and deactivate the UV light 116 during determined occupied time periods.

As another example factor by which a building automation system 100 may control UV lighting, the UV light control engine 104 may account for an actual location of the patient, e.g., as tracked by real-time location data for the patient assigned to the patient room 110. Hospitals or other medical facilities may include real-time tracking capabilities for admitted patients or other personnel. Example location capture techniques include 802.11 triangulation from access points in a building, Bluetooth beaconing, infrared sensors positioned across the building to track patient movement, and ultrasound or ultra-high frequency wireless tracking systems.

In the example shown in FIG. 1, the hospital 106 includes the patient real-time location (RTL) system 124 that stores patient RTL data 128. Although shown separately, the patient RTL system 124 may be implemented as a component or sub-system of the patient information management system 122.

The disinfection environment tracking engine 102 may access the patient RTL data 128 for a patient assigned to the patient room 110, and the UV light control engine 104 may control operation of the UV light 116 based on the accessed patient RTL data 128. For instance, the UV light control engine 104 may automate activation of the UV light 116 during an unoccupied time period of the patient room 110 determined from the patient treatment schedule 126. In such instances, the UV light control engine 104 may use the patient RTL data 128 (and additionally or alternatively use an occupancy status accessed from the occupancy sensor 112) to confirm that the patient is no longer present in the patient room 110 during the unoccupied time period. Put another way, the UV light control engine 104 may confirm, via the patient RTL data 128, that the patient is not present in the patient room 110 during determined unoccupied time periods and, in response, activate the UV light 116 to disinfect the patient room.

As another example use of the patient RTL data 128, the UV light control engine 104 may activate the UV light 116 when a patient is at least a threshold distance away from the patient room 110 and deactivate the UV light 116 otherwise. To illustrate, the UV light control engine 104 may enforce an activation criterion that activates the UV light 116 only when the patient is at least 10 feet (or any other configurable distance) from the patient room 110. Responsive to a determination that the patient is less than 10 feet from the patient room 110 (e.g., returning to the patient room 110 after a scheduled treatment), the UV light control engine 104 may deactivate the UV light 116.

As described above, the UV light control engine 104 may control operation of the UV light 116 to account for occupancy of the patient room 110. Actual or predicted (e.g., scheduled) occupancy may be determined in various ways, and the disinfection environment tracking engine 102 may access environment data, patient data, or any other data relevant or otherwise related to patient room occupancy.

The UV light control engine 104 may utilize any of the described environment or patient data alone to control UV light operation. For instance, the UV light control engine 104 may use one of the occupancy status data extracted from the occupancy sensor 112, the unoccupied time periods extracted from the patient treatment schedule 126, or the patient location information tracked by the patient RTL data 128 as a sole condition or factor in activation and deactivation of the UV light 116. Alternatively, the UV light control engine 104 may use any of the accessed environment or patient data in combination to set automated activations of the UV light 116. For scheduled unoccupied time periods as determined from treatment schedules or other data sources, the UV light control engine 104 may activate the UV light 116 upon confirmation that the patient room 110 is actually unoccupied, e.g., as confirmed via the occupancy sensor 112, the patient RTL data 128 or both. For occupied time periods in which the patient is not scheduled to be outside the patient room 110, the UV light control engine 104 may opportunistically activate the UV light when the occupancy sensor 112 or patient RTL data 128 indicates the patient has left the patient room 110 or the patient room 110 is otherwise unoccupied.

Other automated settings may likewise be applied by the UV light control engine 104 to operate the UV light 116. For instance, a user (e.g., a system administrator) may schedule preset times during which the UV light 116 is activated. Such preset scheduling may correspond to a disinfection cycle or cleaning schedule set up by a medical facility. The UV light control engine 104 may effectuate the preset schedules by interfacing with the UV light controller 118 to activate the UV light 116 during the scheduled disinfection times. During these scheduled disinfection times (or any other time the UV light 116 is activated), the UV light control engine 104 may override the activation based on a detected room occupancy, e.g., by immediately deactivating the UV light 116 responsive to a change in occupancy status as detected by the occupancy sensor 112, when the patient RTL data 128 indicates the patient is occupying the patient room 110, or is within a threshold distance from the patient room 110.

As yet another example, the UV light control engine 104 may control operation of the UV light 116 by activating the UV light 116 responsive to a patient discharge or transfer. For instance, the disinfection environment tracking engine 102 may obtain discharge/transfer data from the patient information management system 122, which may specify a time when the patient assigned to the patient room 110 will be or has been discharged. Responsive to such a discharge/transfer determination, the UV light control engine 104 may schedule a UV light activation for the patient room 110 subsequent to the patient discharge/transfer (e.g., immediately subsequent or subsequent by a configured timing offset). Similarly, as described above, the UV light control engine 104 may override the scheduled UV light activations upon detecting the patient room 110 is occupied.

In many of the examples described above, the UV light control engine 104 triggers activation or deactivation the UV light 116 to disinfect the patient room 110. As another feature, the UV light control engine 104 may control operation of the UV light 116 by setting any number of operation parameters of the UV light 116. For example, the UV light control engine 104 may calibrate the light intensity of the UV light 116, otherwise modulate between different light intensities, or otherwise configure any operation parameter of the UV light 116. For these embodiments, parameter control, UV light activation and deactivation, and other control of the UV light 116 may be specified through control instructions sent by the UV light control engine 104, e.g., the control instructions 136 shown in FIG. 1.

The UV light control engine 104 may configure operation of the UV light 116 according to a determined available disinfection period in which the patient room 110 is expected to or predicted to be unoccupied. The UV light control engine 104 may determine an available disinfection period based on accessed patient treatment schedules 126, for example, or according to any other schedule extraction techniques to identify preset times in which the patient is not scheduled to occupy the patient room 110. That is, the UV light control engine 104 may treat a determined unoccupied time period as an available disinfection period, though other ways to determine an available disinfection period are possible as well.

As another example of available disinfection period determination, the UV light control engine 104 may correlate a patient distance from the patient room 110 to a baseline (e.g., minimum) available disinfection period. The UV light control engine 104 may, for instance, convert a patient distance from the patient room 110 into a minimum available disinfection period based on the walking or transportation speed for a patient to return to the patient room 110. To provide a concrete illustration, the UV light control engine 104 may determine an available disinfection period of at least 45 seconds when the patient is at least 100 feet from the patient room 110. Various distance-to-timing translations may be used, for example based on tiered distance translations (e.g., 20-40 feet away=8 seconds of available disinfection period, 40-80 feet away=20 seconds of available disinfection period, etc.)

As yet another illustration, the UV light control engine 104 may identify a particular available disinfection period based on the patient reaching or being at a particular location, e.g., as determined from the patient RTL data 128. For instance, the patient RTL data 128 may indicate the patient has reached a particular medical facility or room that requires a threshold amount of time for treatment (e.g., an MRI or CT scanning room, surgery room, delivery room, intensive care unit, etc.). In such cases, the UV light control engine 104 may identify a correlated available disinfection period for the patient location, which may be specified in a correlation table or other configurable data structure.

The UV light control engine 104 may adjust, customize, optimize, or intelligently automate operation of the UV light 116 based on determined available disinfection periods. In some examples, the UV light control engine 104 may reduce the UV light intensity of the UV light 116 to reduce energy consumption during an available disinfection period of the patient room 110 (e.g., determined as an unoccupied time period) such that the UV light 116 is nonetheless effective to disinfect the patient room 110 during the available disinfection period.

In other examples, the UV light control engine 104 may deactivate the UV light 116 during the available disinfection period due to a disinfection cycle completing prior to the available disinfection period ending. Such a scenario may occur in which the patient is away from the patient room 110 for an extended period of time, upon which the UV light control engine 104 may reduce resource consumption and lighting costs by deactivating the UV light 116 once a sufficient amount of UV disinfection has occurred.

For some embodiments, another factor by which the UV light control engine 104 may activate or calibrate operation of the UV light 116 is patient medical conditions. FIG. 1 shows an example of UV light control by a building automation system based on patient room data, real-time location data of a patient, and medical data of a patient. The disinfection environment tracking engine 102 accesses medical data of a patient, through which the UV light control engine 104 may activate or calibrate operation of the UV light 116 to disinfect the patient room 110. Example medical data accessible by the disinfection environment tracking engine 102 includes the current medical conditions(s) of a patient, infection capabilities of medical conditions, disease treatment methods, patient medical history, and more.

In FIG. 1, the patient information management system 122 stores medical data in the form of electronic medical records 130 for a patient assigned to the patient room 110. The disinfection environment tracking engine 102 may retrieve the electronic medical records 130 for the patient and the UV light control engine 104 may adapt control of the UV light 116 for the patient room 110 based on the accessed electronic medical records 130.

In a general sense, the UV light control engine 104 may tailor UV light operation for the patient room 110 to specifically address particular medical conditions or disease capabilities the patient room 110 is exposed to. As particular examples, the UV light control engine 104 may account for a contagiousness level or disease spreading capabilities of medical conditions that afflict the patient of the patient room 110. The UV light control engine 104 may increase the UV light intensity or activation UV disinfection times of the UV light 116 for severe or highly contagious medical conditions (e.g., airborne pathogens or life-threatening bacteria) or reduce UV operation parameters for medical conditions of lesser severity or contagiousness level (e.g., common cold, or non-infectious medical conditions).

In some implementations, the UV light control engine 104 may access disinfection parameters for specific diseases, medical conditions, or ailments from medical databases. The center for disease control (CDC), research facilities, or other healthcare agencies may provide treatment recommendations or parameters for various medical conditions, and the building automation system 100 may access any such treatment parameters to calibrate the UV light 116. Such parameters may specify best-practices or recommended disinfection parameters, including UV light intensities and UV disinfection times to effectively eradicate infectious bacteria and diseases.

The UV light control engine 104 may determine a disinfection time (or active disinfection time), which may refer to a baseline or minimum time period to activate the UV light 116 to disinfect the patient room 110. Put another way, the UV light control engine 104 may determine the disinfection time as the required time period needed to effectively disinfect the patient room 110 through activation of the UV light 116. Determination of the disinfection time may be performed as a function of the UV light capabilities of the UV light 116 (e.g., maximum intensity), severity of a medical condition exposed to the patient room 110, length of time that the patient has occupied the patient room 110 prior to disinfection, and various other factors. The more severe the medical condition and the longer the patient has occupied the patient room 110 prior to UV light activation, the longer the disinfection time that the UV light control engine 104 may determine. Various weights may be applied to each factor in the disinfection time determination, which may be configurable based on UV disinfection goals (e.g., healthcare associated infections reduction, UV light costs, efficiency, patient traffic, etc.).

As one example, the UV light control engine 104 may determine a disinfection time for the patient room 110 based on a severity of the medical condition of the patient and a length of an occupied time period in an occupancy schedule (e.g., the patient treatment schedule 126) in which the patient occupies the patient room 110. The UV light control engine 104 may further identify an unoccupied time period in the occupancy schedule in which the patient does not occupy the patient room and activate the UV light 116 to disinfect the patient room 110 during the unoccupied time period responsive to a determination that a length of the unoccupied time period exceeds the determined disinfection time. When the determined disinfection time exceeds (i.e., is longer than) the unoccupied time for the patient room 110, the UV light control engine 104 may operate the UV light 116 with increased intensity or, alternatively, determine not to activate the UV light 116 at all (e.g., as a determination that the unoccupied time period is too short to effectively disinfect the patient room 110 and UV light activation would result in inefficient resource consumption).

When the UV light control engine 104 identifies a determined disinfection time is shorter than an unoccupied time period, the UV light control engine 104 may operate the UV light 116 in various ways. In some instances, the UV light control engine 104 may activate the UV light 116 for a length of time equal to the determined disinfection time and deactivate the UV light 116 afterwards. Doing so may reduce resource consumption by turning off the UV light 116 after effective UV light disinfection has been achieved. In other instances, the UV light control engine 104 may reduce a light intensity of the UV light 116 to reduce energy consumption during the unoccupied time period of the patient room 110 such that the UV light 116 is nonetheless effective to disinfect the patient room for the length of the unoccupied time period based on the medical condition of the patient. Other calibration or activation options are possible as well. For these embodiments, such control of the UV light 116 may be effectuated by the UV light control engine 104 through the control instructions 136 generated and sent to the UV light controller 118.

Thus, the UV light control engine 104 may adapt operation of the UV light 116 to account various susceptible environment and patient-based factors. While some examples are described herein, the UV light control engine 104 may account for any number of additional or alternative factors in controlling the activation, deactivation, disinfection duration, and UV intensity of the UV light 116 in disinfecting the patient room 110.

FIG. 1 further shows embodiments of UV light control and room access control by a building automation system 100. As another feature of UV light control, the building automation system 100 may limit access to a susceptible environment undergoing UV light disinfection. The UV light control engine 104 may interface with the hospital access systems to control access to the patient room 110 during UV light operation to reduce or prevent inadvertent exposure to the UV light 116 when activated.

In particular, the hospital 106 shown includes a physical access control system 132. The physical access control system 132 may be any system, logic, hardware, or physical elements that control access to building spaces within the hospital 106. As such, the physical access control system 132 may support room lockdowns, gated entries, badge security, or support other access control mechanisms in the hospital 106. For the patient room 110, the physical access control system 132 may have access limitation capabilities to lock or unlock the door 114 of the patient room 110.

The UV light control engine 104 may limit access to the patient room 110 upon activation of the UV light 116. Prior to, concurrent with, or directly subsequent to activation of the UV light 116, the UV light control engine 104 may cause the physical access control system 132 to deny access to the patient room 110, doing so to prevent human exposure to UV light. In some examples, the UV light control engine 104 may send a lock request 134 to a physical access control system 132 to lock the door 114 of the patient room 110 when the UV light 116 is active to disinfect the patient room. In some instances, the UV light control engine 104 sends a one-sided lock request to the physical access control system 132 to deny exterior entry to the patient room 110 but allowing interior exiting from the patient room 110. Responsive to such a request, the physical access control system 132 may lock the door 114 from outside access but allow for exiting of the patient room 110 through the door 114, e.g., in case the patient or another person is located within the patient room 110 upon activation of the UV light 116.

In some instances, the UV light control engine 104 may issue an alarm warning prior to activation of the UV light 116. The alarm warning may cause an acoustic or visual warning to be issued in the patient room 110 prior to activation of the UV light 116, e.g., via an alarm system or sound system of the hospital 106. Upon deactivation of the UV light 116, the UV light control engine 104 may send an unlock request to the physical access control system 132. In some instances, the UV light control engine 104 sends the unlock request after a threshold amount of time has elapsed since deactivation of the UV light 116, providing another measure of safety. Accordingly, the building automation system 100 may provide various safety features to reduce or prevent human exposure to the UV light 116 during active UV disinfection periods. The building automation system 100 may do so in combination with intelligent control of the UV light 116 (e.g., as effectuated through control instructions 136) to disinfect various susceptible environments).

Figure 2:
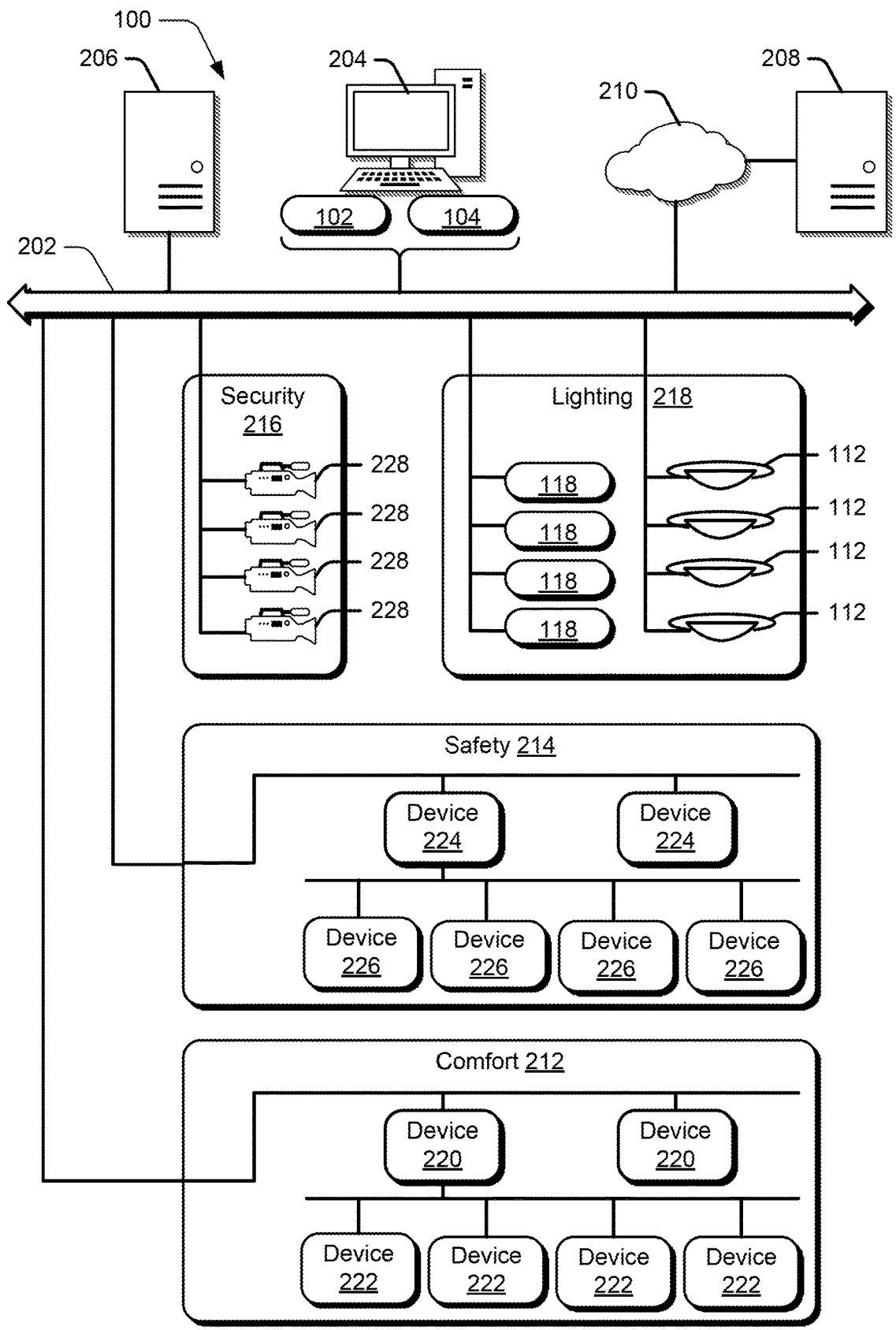
FIG. 2 represents an example of the building automation system of FIG. 1 that supports intelligent control of UV lights to disinfect susceptible environments based on occupant density.

Referring to FIG. 2, there is shown is a block diagram representing an example implementation of the building automation system. The building automation system 100 is an environmental control system configured to control one or more environmental parameters for a building, such as temperature, humidity, ventilation, lighting, fire safety, security, and the like. For example, the building automation system 100 may comprise one or more network connections or buses 202 to connectivity for the system. For one embodiment, the example building automation system 100 may comprise one or more management devices, such as a management workstation 204, a management server 206, or a remote management device 208 connecting through a wired or wireless network connection 210, that allows the setting and/or changing of various controls of the system. For example, the management devices 204, 206, 208 include the disinfection environment tracking engine 102 and the UV light control engine 104 to provide intelligent control of UV lights to disinfect designated areas based on occupant density. While a brief description of the building automation system 100 is provided below, it will be understood that the building automation system 100 described herein is only one example of a particular form or configuration for a building automation system and that the system 100 may be implemented in any other suitable manner without departing from the scope of this disclosure.

The management devices 204, 206, 208, are configured to provide overall control and monitoring of the building automation system 100. For the illustrated embodiment of FIG. 4, the building automation system 100 provides connectivity to subsystems for various environmental parameters such as components of comfort systems 212, safety systems 214, security systems 216, and lighting systems 218. For example, comfort systems 212 may include various devices 220, 222 for monitoring and controlling heating, cooling, and ventilation of areas within a building or group of buildings. Examples of comfort devices include, but are not limited to, stations, field panels, field controllers, field devices, and the like. Some devices 220 may communicate directly with a network connection or bus 202, whereas other devices 222 may communicate through, and perhaps be controlled by, another device. Similarly, safety systems 214 may include various devices 224, 226 for monitoring and controlling fire protection for areas within a building or a group of buildings. Examples of safety devices include, but are not limited to controllers, control panels, detectors, alarm systems, video surveillance cameras, and the like. Similar to comfort devices, some safety devices 224 may communicate directly with a network connection or bus 202, whereas other safety devices 226 may communicate through, and perhaps be controlled by, another device. As stated above, the illustrated embodiment of the building automation system 100 may provide southbound connectivity to subsystems 228 for security systems 216 and other systems, such as video surveillance cameras and motion detectors, for monitoring and controlling various areas within a building or a group of buildings.

The lighting systems 218 may include various devices 220, 222 for monitoring and controlling illumination of areas within a building or group of buildings. Examples of lighting devices include, but are not limited to, lighting sensors such as occupancy sensors 112, lighting controllers such as UV light controllers 118, lighting switches, lighting gateways, lighting hubs, lighting servers, and the like. Occupancy sensors include, but are not limited to, light sensors, motion sensors, temperatures sensors, image sensors (such as still and video images), and air quality sensors. Lighting controllers may be connected to, or integrated with, light fixtures of a particular area. Similar to the comfort, safety, and security devices, lighting devices may communicate directly with a network connection or bus 202, and/or through, and perhaps be controlled by, another device. The lighting system 218 may include legacy or 3rd party devices to be coupled to other devices of the building automation system 100. It is to be understood that the system 100 may comprise any suitable number of any of components 112, 118, 220-226 based on the particular configuration for each building or group of buildings.

Figure 3:
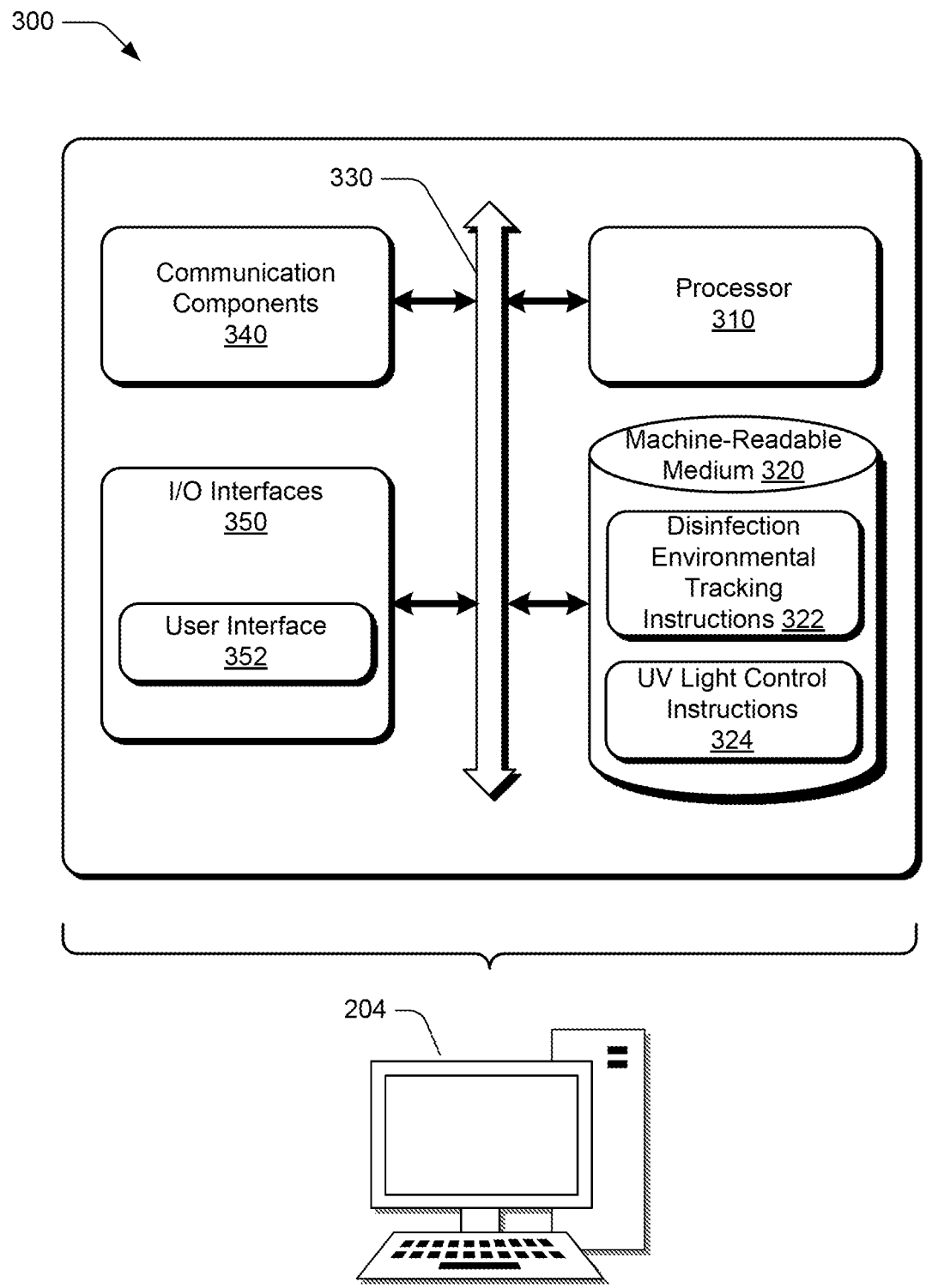
FIG. 3 represents an example of a device of the building automation system of FIG. 2 that supports intelligent control of UV lights to disinfect susceptible environments based on occupant density.

FIG. 3 shows an example of a management device 300, such as management devices 204, 206, 208, that supports control of UV lights to disinfect patient rooms or other susceptible environments based on occupant density. The management device 300 represents one or more components of the building automation system. The management device 300 may include a processor 310, which may take the form of a single or multiple processors. The processor(s) 310 may include a central processing unit (CPU), microprocessor, or any hardware device suitable for executing instructions stored on a machine-readable medium. The management device 300 may include a machine-readable medium 320. The machine-readable medium 320 may take the form of any non-transitory electronic, magnetic, optical, or other physical storage device that stores executable instructions, such as the disinfection environment tracking instructions 322 and the UV light control instructions 324 shown in FIG. 3. As such, the machine-readable medium 320 may be, for example, Random Access Memory (RAM) such as a dynamic RAM (DRAM), flash memory, spin-transfer torque memory, an Electrically Erasable Programmable Read-Only Memory (EEPROM), a storage drive, an optical disk, and the like.

The management device 300 may execute instructions stored on the machine-readable medium 320 through the processor 310. Executing the instructions may cause the management device 300 (e.g., a building automation system or one or more components thereof) to perform any of the UV light control features described herein, including according to any of the features with respect to the building automation system 100, the disinfection environment tracking engine 102, the UV light control engine 104, or combinations thereof. For example, execution of the disinfection environment tracking instructions 322 by the processor 310 may cause the management device 300 to access patient room data indicative of a state of a patient room of a patient, the patient room data including an occupancy schedule for the patient room that indicates an unoccupied time period during which the patient does not occupy the room and access medical data of the patient, the medical data of the patient specifying a medical condition of the patient. Similarly, the management device 300 may access health information indicative of a state of facility personnel, maintenance, disease, and health care services. For example, the health information may include an occupancy schedule for a doctor, nurse, or maintenance person that indicates time periods when the facility personnel occupies or does not occupy the area.

Execution of the UV light control instructions 324 by the processor 310 may cause the management device 300 to control operation of UV light to disinfect the patient room based on the patient room data and the medical condition of the data, including by calibrating the UV light to account for a length of the unoccupied time period and a severity of the medical condition of the patient.

The components of the management device 300 comprise a communication data bus 330 and communication components 340. The communication components 340 may utilize wired or wireless technology to communicate directly or indirectly with a communication network, such as the Internet. The communication components 340 of the device components may utilize wired technology for communication such as any type of transmission of data over a physical conduit, such as an electrical cable or optical fiber cable. The communication component 340 of the device components may utilize wireless technology, in addition to or in the alternative to wired technology, such as, but are not limited to, satellite-based and cellular-based communications and their variants as well as wireless local area network (WLAN) communication and their variants, such as infrastructure, peer-to-peer, ad hoc, bridge, and wireless distribution based communications. Examples of WLAN communications include, but are not limited to, IEEE 802.11 (Wi-Fi), IEEE 802.16 (WiMAX), Bluetooth, BLE, and ZigBee. Wireless technology may further include other forms of communication such as microwave or infrared technology (IR).

The I/O interfaces 350 of the device components may include various types of video, audio, and/or mechanical input components. Examples of input components include, but are not limited to, keyboard, mouse, touchscreen, touchpad, microphone, and other types of sensors. Examples of output components include, but are not limited to, displays, speakers, touchscreen, vibrators, and other types of indicators. The I/O interfaces 350 of the device components may also include a user interface 352 that is a subset of I/O interfaces for interaction with a user, installer, or technician of the device.

Figure 4:
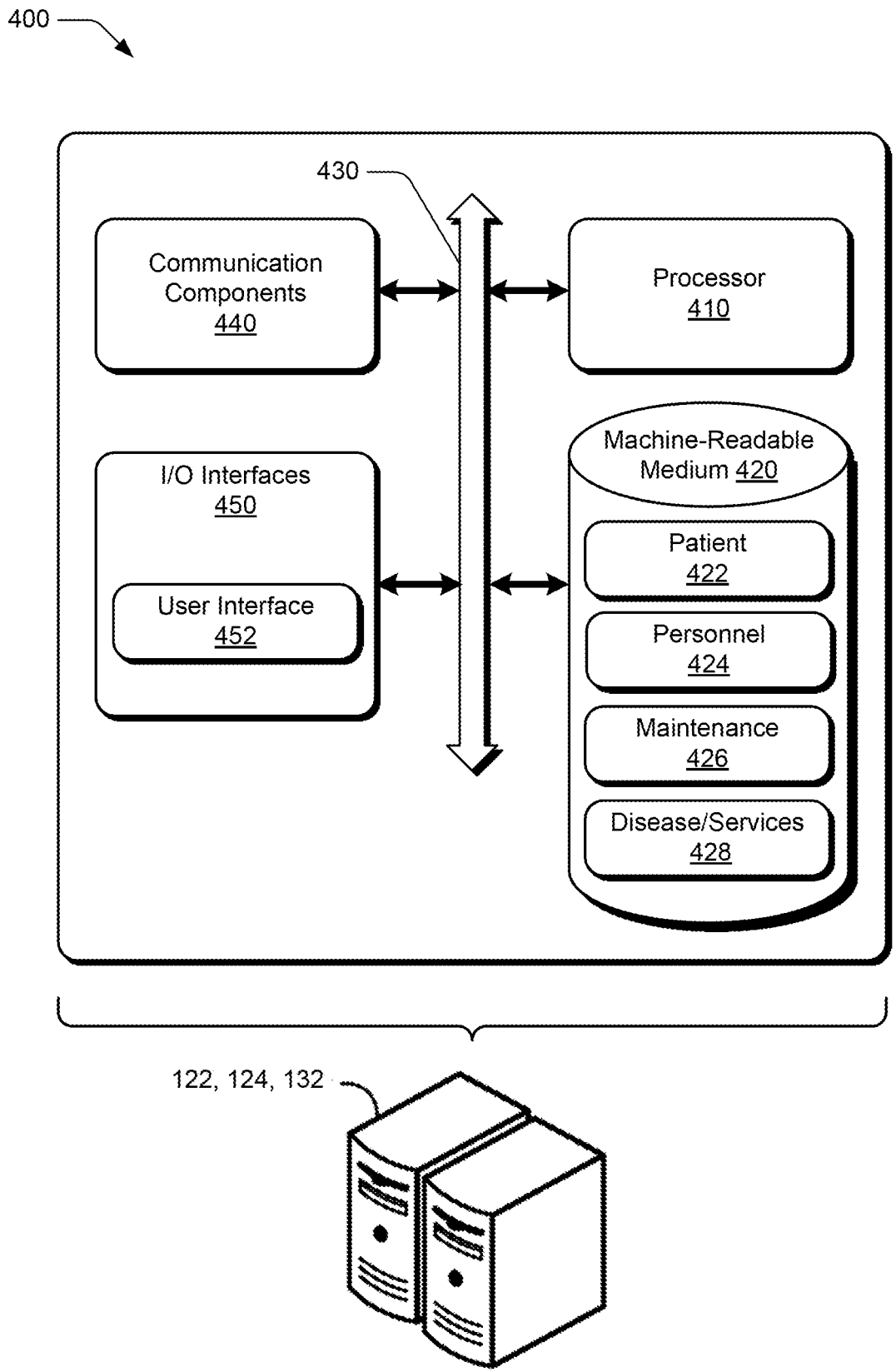
FIG. 4 represents an example of the health information system of FIG. 1 that supports the building automation system to control intelligently UV lights to disinfect susceptible environments based on occupant density.

FIG. 4 shows an example of a health information system 400, such as systems 122, 124, 132 or a combination thereof, that provides further support for control of UV lights to disinfect patient rooms or other susceptible environments based on occupant density. The system 400 may include a processor 410 and a machine-readable medium 420 similar to the corresponding components of the management device 300. The machine-readable medium 420 may take the form of any non-transitory electronic, magnetic, optical, or other physical storage device that stores executable instructions, such as the patent information 422, facility personnel information 424, maintenance information 426, and disease and health care services information 428 shown in FIG. 4.

The system 400 may execute instructions stored on the machine-readable medium 420 through the processor 410. Executing the instructions may cause the system 400 (e.g., the patient information management system 122, the patient real time location system 124, and/or the physical access control system 132) to provide support for any of the UV light control features described herein, including according to any of the features with respect to the building automation system 100. For example, the building automation system 100 may optimize an operation for disinfection based on real time information of occupant density and the nature of services at a particular area or location, as well as knowledge of known occupants within the area or location.

For some embodiments, the system 400 may provide to the building automation system 100 information about the nature of health and sickness at the location where occupancy is measured. For example, the system 400 may provide patient information 422 to the building automation system 100 that identifies the nature and/or sickness of the patient, including the location and time periods of occupation in the designated area. As another example, the system 400 may provide disease and health care services information 428, which may be stored at a disease database of the system, that identifies the nature and/or sickness of one or more occupants other than the patient, including the location and time periods of occupation in the designated area.

For some embodiments, the system 400 may provide to the building automation system 100 personnel information 424 about personnel or visitors of the facility that may be associated with the patient and/or the designate area during particular time periods. For example, the system 400 may provide personnel information 424 about doctors, nurses, staff (including administrators), and/or visitors, including the location and time periods of occupation in the designated area. As another example, the system 400 may provide scheduling information about personnel or visitors of the facility, such as expected time periods when a doctor is expected to review the patient, a nurse is expected to check on the patient, or visitation hours available to a visitor.

For some embodiments, the system 400 may provide to the building automation system 100 maintenance information 426 about maintenance people associated with the patient and/or the designated area during particular time periods. For example, the system 400 may provide maintenance information 426 about cleaning personnel and/or facility maintenance personnel, including the location and time periods of occupation in the designated area. As another example, the system 400 may provide scheduling information about cleaning personnel and/or facility maintenance personnel with regard to regular, periodic visits or special, requested visits to the designated area.

The components of the health information system 400 comprise a communication data bus 430, communication components 440, and I/O interfaces 450. The communication components 440 may utilize wired or wireless technology to communicate directly or indirectly with a communication network, such as the Internet, similar to the management device 300. The I/O interfaces 450 of the device components may include various types of video, audio, and/or mechanical input components. Examples of input components include, but are not limited to, keyboard, mouse, touchscreen, touchpad, microphone, and other types of sensors. Examples of output components include, but are not limited to, displays, speakers, touchscreen, vibrators, and other types of indicators. The I/O interfaces 450 of the device components may also include a user interface 452 that is a subset of I/O interfaces for interaction with a user, installer, or technician of the device.

Figure 5:
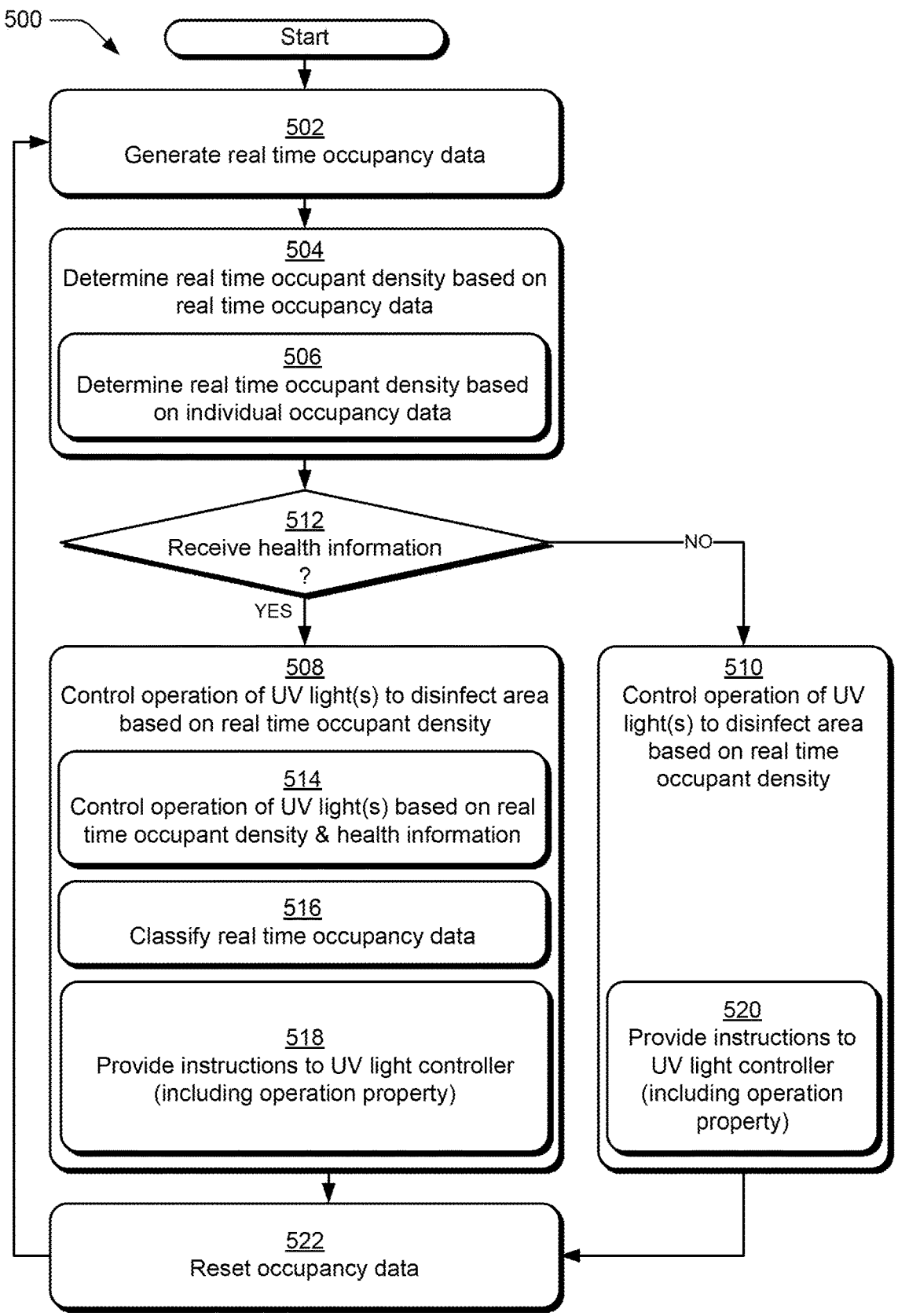
FIG. 5 represents an example of logic that the health environment system of FIG. 1, including the building automation system of FIG. 2, may implement to support intelligent control of UV lights to disinfect susceptible environments based on occupant density.

FIG. 5 shows an example of logic 500 that a system, such as the building automation system 100, may implement to support control of UV lights to disinfect patient rooms based on occupant density. For example, the building automation system 100 may implement the logic 500 as hardware, executable instructions stored on a machine-readable medium, or as a combination of both. The building automation system 100 may implement the logic 500 through the disinfection environment tracking engine 102 and the UV light control engine 104, through which the building automation system 100 may perform or execute the logic 500 as a method to control UV lights for room disinfection. The following description of the logic 500 is provided using the disinfection environment tracking engine 102 and the UV light control engine 104 as examples. However, various other implementation options by the building automation system 100 are possible.

The logic 500 of the system, such as the building automation system 100, includes generating 502 real time occupancy data 120 associated with multiple objects detected within an area. For example, multiple occupancy sensors 112 at the area may generate the occupancy data 120, in real time, based on the objects detected within the area. Examples of an area with multiple occupancy sensors include, but are not limited to, a room, a floor of a building, a hallway, a partitioned area, an open room, or other designated area. The occupancy data 120 is generated in real time such that the input data is processed within seconds, or milliseconds, so that it is available virtually as soon as possible as feedback. It should be noted that people or occupants may be referred to as objects herein because the building automation system and its components may identify a person or occupant as a type of object.

In accordance with the logic 500, the system may next determine 504 real time occupant density of the multiple objects detected within the area based on the real time occupancy data 120 generated by the multiple occupancy sensors 112. For some embodiments, the real time occupancy data generated 502 by the multiple occupancy sensors 112 may include individual occupancy data corresponding to a presence within the area by each object of detected by the multiple occupancy sensors. Thus, the disinfection environment tracking engine 102 may determine 506 the real time occupant density based on the individual occupancy data associated with the multiple objects.

The disinfection environment tracking engine 102 may determine 504 real time occupant density from the real time occupancy 120 data using various methods. For some embodiments, the system may receive data from the sensors, group the data according to identified groupings of the sensors, and determine real time occupant density based on data analytics processing of one or more of the groups of sensed data. For other embodiments, the system may group sensed data according to one or more identified areas, perform data analytics every sampling period, and perform the data analytics processing on the sensed data. These other embodiments may also determine a level of certainty of the number of occupants within the designated area. For yet other embodiments, the system may generate samples of the sensed data based on a particular sampling criterion, apply a time-weighting to the samples over a sampling interval, determined a weighted average by averaging the time-weighted samples over the sampling period, and estimate a number of occupants based on the multiple weighted averages. These yet other embodiments may also determine a level of certainty of the number of occupants based on the multiple weighted averages.

After determining the real time occupant density, the system then controls 508, 510 operation of one or more ultraviolet (UV) lights based on the real time occupant density determined by the disinfection environment tracking engine 102. The ultraviolet light control engine 104 may send control instructions 136 to UV light controller 118, which is coupled to the UV light 116, to control the disinfect the area. The ultraviolet light control engine 104 may control 508, 510 one or more operation properties of the UV light or lights such as operation time, operation duration, operation frequency, or operation power for each UV light. For example, the UV light controller 118 may manage the power, frequency, timing, and/or duration emitted to the designated area by UV light 116 based on the control instructions 136 receive from the ultraviolet light control engine 104. In this regard, the power of the UV light 116 is based on the energy strength of emission, the frequency of the UV light is based on the pulse per unit time of emission, the timing of the UV light is based on the activation time of emission, and the duration of the UV light is based on the difference between the ending and starting times of emission. Accordingly, the system may adjust the strength, pulsation, activation time, time period, or combination thereof, for UV light emission.

The system may receive health information from a health information system for some embodiments, may not receive the health information for other embodiments, or may or may not receive the health information based on the system configuration and/or availability of the health information. For example, as represented by FIG. 5, the system may detect or determine 512 whether health information has been received from a health information system. If health information is received, then the system may control 508 operation of one or more UV lights 116 based on the received health information as well as the real time occupant density. If health information is not received, then the system may control 510 operation of one or more UV lights 116 based on the real time occupant density without consideration of health information from any type of health information system.

In response to receiving health information, the system may provide further support for control of UV lights to disinfect patient rooms or other susceptible environments based on occupant density in conjunction with the health information. In particular, the system may control 508, 514 operation of one or more UV lights 116 based on health information received from the health information system and the real time occupant density. Examples of a health information system include, but are not limited to, the patient information management system 122, the patient real time location system 124, the physical access control system 132, or a combination thereof, as described above in reference to FIG. 1. For example, the building automation system 100 may receive 512 the health information from the health information system in response to, or otherwise subsequent to, determining 504 the real time occupant density. Thereafter, when controlling 508 operation of the UV light, the UV light control engine 104 may control 514 the UV light controller 118, and thus, the UV light 116, based on the real time occupant density and the health information.

As described above, the building automation system 100 receive health information from one or more health information systems and, thus, access the health information indicative of a state of facility personnel, maintenance, disease, and health care services. For example, the health information may include one or more scheduled events associated with the occupant(s) and the designated area. For this example, the health information may include an occupancy schedule for a doctor, nurse, or maintenance person that indicates time periods when the facility personnel occupies or does not occupy the area. For some embodiments, the health information system may provide to the building automation system 100 information 422, 428 about the nature of health and sickness at the location where occupancy is measured. The ability to disinfect a susceptible environment by the building automation system 100 may be enhanced with knowledge about the nature of a facility and the known groups of potential occupants at the designated area. For example, the business automation system 100 make lookup, with or without the health information system, a disease database and determine the strength of UV treatment necessary to inactivate or otherwise impact infectious entities, thus optimizing the strength and time for the disinfect operation. For some embodiments, the health information system may provide to the building automation system 100 personnel information 424 about personnel or visitors of the facility that may be associated with the patient and/or the designate area during particular time periods. For some embodiments, the health information system may provide to the building automation system 100 maintenance information 426 about cleaning and maintenance people associated with the patient and/or the designated area during particular time periods.

The health information from the health information system(s) may include one or more classifications, such as a patient class, a doctor class, a nurse class, a staff class, or a visitor class. One or more objects of the multiple objects (such as occupants) may correspond to a particular classification of multiple classifications. Accordingly, the UV light control engine 104 may classify 516 the real time occupancy data based on the classifications of the objects detected by the occupancy sensors within the designated area. Other examples of classifications included in the health information of the health information system include, but are not limited to, a disease class indicating a disease exposed to the area, or a service class indicating some or all of the control operation of the UV light 116 to disinfect the area based on a disease exposed to the area.

For some embodiments, the UV light control engine 104 may adjust the strength and duration of UV treatment based on an estimated break down of occupants in the designated area to be disinfected since the last time the designated area was disinfected. The strength may be based on the combination (such as a summation of strength values) of two or more classifications, such as a combination of a patient class, a doctor class, a nurse class, a staff class, and a visitor class, in which each class includes a quantity of members of the class and a UV strength required to disinfect for each particular class. In such case, the time to disinfect is based on the UV strength and a device effectiveness. The device effectiveness is based on a measurement of time required for the UV light 116 to achieve a certain level of disinfection.

The ultraviolet light control engine 104 may provide 518, 520 control instructions 136 to UV light controller 118, which is coupled to the UV light 116, to control the disinfect the area. The control instructions 136 provided 518, 520 by the ultraviolet light control engine 104 may include one or more operation properties of the UV light or lights such as operation time, operation duration, operation frequency, or operation power for each UV light. The system may provide 518 control instructions in response to receiving 512 health information or the system may provide 520 the control instructions without receiving 512 health information from any type of health information system. In either case, the system may continue operation after providing the control instructions, such as resetting 522 occupancy data after the area is disinfected and returning to the generation 502 of real time occupancy data 120 associated with multiple objects detected within an area.

For some embodiments, the UV light control engine 104 may adjust the strength and time of UV treatment based on an estimated total number of occupants in the designated area to be disinfected since the last time the area was disinfected. The strength of the UV treatment by the UV light 116 may be based on the number of occupants from the last time the designated area was disinfected. The time to disinfect for the UV treatment may be based on the strength and a device effectiveness. The device effectiveness may be based on a measurement of time required for the UV light 116 to achieve a certain level of disinfection.

The systems, methods, devices, and logic described above, including the building automation system 100, the disinfection environment tracking engine 102, and the UV light control engine 104, may be implemented in many different ways in many different combinations of hardware, logic, circuitry, and executable instructions stored on a machine-readable medium. For example, the building automation system 100, the disinfection environment tracking engine 102, the UV light control engine 104, or combinations thereof, may include circuitry in a controller, a microprocessor, or an application specific integrated circuit (ASIC), or may be implemented with discrete logic or components, or a combination of other types of analog or digital circuitry, combined on a single integrated circuit or distributed among multiple integrated circuits. A product, such as a computer program product, may include a storage medium and machine readable instructions stored on the medium, which when executed in an endpoint, computer system, or other device, cause the device to perform operations according to any of the description above, including according to any features of the building automation system 100, the disinfection environment tracking engine 102, the UV light control engine 104, or combinations thereof.

The processing capability of the systems, devices, and engines described herein, including the building automation system 100, the disinfection environment tracking engine 102, and the UV light control engine 104, may be distributed among multiple system components, such as among multiple processors and memories, optionally including multiple distributed processing systems or cloud/network elements. Parameters, databases, and other data structures may be separately stored and managed, may be incorporated into a single memory or database, may be logically and physically organized in many different ways, and may implemented in many ways, including data structures such as linked lists, hash tables, or implicit storage mechanisms. Programs may be parts (e.g., subroutines) of a single program, separate programs, distributed across several memories and processors, or implemented in many different ways, such as in a library (e.g., a shared library).

Those skilled in the art will recognize that, for simplicity and clarity, the full structure and operation of all systems suitable for use with the present disclosure are not being depicted or described herein. Also, none of the various features or processes described herein should be considered essential to any or all embodiments, except as described herein. Various features may be omitted or duplicated in various embodiments. Various processes described may be omitted, repeated, performed sequentially, concurrently, or in a different order. Various features and processes described herein can be combined in still other embodiments as may be described in the claims.

It is important to note that while the disclosure includes a description in the context of fully functional systems, those skilled in the art will appreciate that at least portions of the mechanism of the present disclosure are capable of being distributed in the form of instructions contained within a machine-usable, computer-usable, or computer-readable medium in any of a variety of forms, and that the present disclosure applies equally regardless of the particular type of instruction or signal bearing medium or storage medium utilized to actually carry out the distribution. Examples of machine usable/readable or computer usable/readable mediums include: nonvolatile, hard-coded type mediums such as read only memories (ROMs) or erasable, electrically programmable read only memories (EEPROMs), and user-recordable type mediums such as floppy disks, hard disk drives and compact disk read only memories (CD-ROMs) or digital versatile disks (DVDs).

Although an example embodiment of the present disclosure has been described in detail, those skilled in the art will understand that various changes, substitutions, variations, and improvements disclosed herein may be made without departing from the spirit and scope of the disclosure in its broadest form.

The invention claimed is:

1. A system comprising:
a plurality of occupancy sensors configure to generate real time occupancy data associated with a plurality of objects detected within an area; and
a building automation system including a disinfection environment tracking engine and an ultraviolet light control engine, wherein:
the disinfection environment tracking engine configured to determine real time occupant density of the plurality of objects detected within the area based on the real time occupancy data generated by the plurality of occupancy sensors; and
the ultraviolet light control engine configured to control operation of at least one ultraviolet light to disinfect the area based on the real time occupant density determined by the disinfection environment tracking engine, wherein the ultraviolet light control engine controls the operation of the at least one ultraviolet light based on health information received from a health information system and the real time occupant density,
wherein the health information received from the health information system comprises a healthcare professional classification selected from a group consisting of a doctor class, a nurse class, or a staff class and a non-healthcare professional classification including a visitor class,
wherein one object of the plurality of objects corresponds to a class of the healthcare professional classification and another object of the plurality of objects corresponds to a class of the non-healthcare professional classification, and
wherein the ultraviolet light control engine controls an operation strength and duration for each ultraviolet light based on a combination of the healthcare professional classification and a non-healthcare professional classification as well as a last time the area was disinfected, including a summation of strength values of two or more classifications, each classification including an ultraviolet strength required to disinfect for each particular classification.

2. The system as described by claim 1, wherein:
the real time occupancy data include individual occupancy data corresponding to a presence within the area by each object of the plurality of objects detected by the plurality of occupancy sensors; and
the disinfection environment tracking engine determines real time occupant density based on the individual occupancy data associated with the plurality of objects.

3. The system as described by claim 1, wherein the ultraviolet light control engine controls at least one operation property of the at least one ultraviolet light selected from the group consisting of operation time, operation duration, or operation frequency for each ultraviolet light.

4. The system as described by claim 1, wherein the health information received from the health information system includes at least one scheduled event associated with an occupant and the area.

5. The system as described by claim 1, wherein the health information received from the health information system includes at least one service class indicating at least a portion of the control operation of the at least one ultraviolet light to disinfect the area based on a disease exposed to the area.

6. A method of a building automation system comprising:
generating, at a plurality of occupancy sensors, real time occupancy data associated with a plurality of objects detected within an area;
determining, at a disinfection environment tracking engine, real time occupant density of the plurality of objects detected within the area based on the real time occupancy data generated by the plurality of occupancy sensors; and
controlling, at an ultraviolet light control engine, operation of at least one ultraviolet light to disinfect the area based on health information received from a health information system and the real time occupant density determined by the disinfection environment tracking engine,
wherein the health information received from the health information system comprises a healthcare professional classification selected from a group consisting of a doctor class, a nurse class, or a staff class and a non-healthcare professional class including a visitor class,
wherein one object of the plurality of objects corresponds to a class of the healthcare professional classification and another object of the plurality of objects corresponds to a class of the non-healthcare professional classification, and
wherein controlling the operation of the at least one ultraviolet light includes controlling an operation strength and duration for each ultraviolet light based on a combination of the healthcare professional classification and a non-healthcare professional classification as well as a last time the area was disinfected, including a summation of strength values of two or more classifications, each classification including an ultraviolet strength required to disinfect for each particular classification.

7. The method as described by claim 6, wherein:
the real time occupancy data include individual occupancy data corresponding to a presence within the area by each object of the plurality of objects detected by the plurality of occupancy sensors; and
determining real time occupant density includes determining the real time occupant density based on the individual occupancy data associated with the plurality of objects.

8. The method as described by claim 6, wherein controlling the operation of the at least one ultraviolet light includes controlling at least one operation property of the at least one ultraviolet light selected from the group consisting of operation time, operation duration, or operation frequency for each ultraviolet light.

9. The method as described by claim 6, wherein the health information received from the health information system includes at least one scheduled event associated with an occupant and the area.

10. The method as described by claim 6, wherein the health information received from the health information system includes at least one service class indicating at least a portion of the control operation of the at least one ultraviolet light to disinfect the area based on a disease exposed to the area.

11. A non-transitory machine-readable medium comprising storing instructions that, when executed by a processor, cause a system to:
   generate real time occupancy data associated with a plurality of objects detected within an area;
   determine real time occupant density of the plurality of objects detected within the area based on the real time occupancy data generated by the plurality of occupancy sensors; and
   control operation of at least one ultraviolet light to disinfect the area based on health information received from a health information system and the real time occupant density determined by the disinfection environment tracking engine,
   wherein the health information received from the health information system comprises a healthcare professional classification selected from a group consisting of a doctor class, a nurse class, or a staff class and a non-healthcare professional class including a visitor class,
   wherein one object of the plurality of objects corresponds to a class of the healthcare professional classification and another object of the plurality of objects corresponds to a class of the non-healthcare professional classification, and
   wherein control of the operation of the at least one ultraviolet light includes control of an operation strength and duration for each ultraviolet light based on a combination of the healthcare professional classification and a non-healthcare professional classification as well as a last time the area was disinfected, including a summation of strength values of two or more classifications, each classification including an ultraviolet strength required to disinfect for each particular classification.

12. The non-transitory machine-readable medium as described by claim 11, wherein:
   the real time occupancy data include individual occupancy data corresponding to a presence within the area by each object of the plurality of objects detected by the plurality of occupancy sensors; and
   the instructions cause the system to determine the real time occupant density based on the individual occupancy data associated with the plurality of objects.

13. The non-transitory machine-readable medium as described by claim 11, wherein the ultraviolet light control engine controls at least one operation property of the at least one ultraviolet light selected from the group consisting of operation time, operation duration, or operation frequency for each ultraviolet light.

14. The non-transitory machine-readable medium as described by claim 11, wherein the health information received from the health information system includes at least one scheduled event associated with an occupant and the area.

* * * * *